(12) United States Patent
Paraschiv et al.

(10) Patent No.: US 11,049,607 B1
(45) Date of Patent: Jun. 29, 2021

(54) SYSTEM AND METHOD FOR FACILITATING PATIENT DISCHARGE WITH THE AID OF A DIGITAL COMPUTER

(71) Applicant: Health Care Solutions Inc., Kirkland, WA (US)

(72) Inventors: Iulian Vladimirovich Paraschiv, Kirkland, WA (US); Michael Anatolyevich Nikitin, Kirkland, WA (US)

(73) Assignee: HEALTH CARE SOLUTIONS INC., Kirkland, WA (US)

( * ) Notice: Subject to any disclaimer, the term of this patent is extended or adjusted under 35 U.S.C. 154(b) by 355 days.

(21) Appl. No.: 15/969,645

(22) Filed: May 2, 2018

Related U.S. Application Data

(60) Provisional application No. 62/500,392, filed on May 2, 2017.

(51) Int. Cl.
*G16H 40/20* (2018.01)
*G16H 10/60* (2018.01)
(Continued)

(52) U.S. Cl.
CPC .............. *G16H 40/20* (2018.01); *G16H 10/60* (2018.01); *H04L 67/1004* (2013.01);
(Continued)

(58) Field of Classification Search
CPC ................................................ H04L 29/08162
See application file for complete search history.

(56) References Cited

U.S. PATENT DOCUMENTS 8,065,167 B1 * 11/2011 Wyman .................. G06Q 50/22
705/3
9,832,069 B1 * 11/2017 Cleveland ......... H04L 29/08162
(Continued)

FOREIGN PATENT DOCUMENTS

WO    2018005828    1/2018

OTHER PUBLICATIONS

What to Look For When Touring a Nursing Home, 2016, Next Avenue (Year: 2016).*

*Primary Examiner* — Aryan E Weisenfeld
*Assistant Examiner* — Karen A Hranek
(74) *Attorney, Agent, or Firm* — Leonid Kisselev

(57) ABSTRACT

Data from a plurality of parties involved in a discharge of the patient is securely processed in a cloud-computing environment. The cloud-computing environment identifies long-term care facilities suitable for the patient using a plurality of matching criteria derived at least in part from discharge information provided by the facility from which the patient is being, contacts the long-term care facilities to determine whether the facilities would be interested to conducting a tour for the patient's representative (and, or alternatively, the patient), and helps facilitate scheduling of the tour. The cloud-computing environment can further identify assessors capable of conducting the medical assessment of the patient and schedule the assessment, providing the assessment to all long-term care facilities. The cloud-computing environment securely stores the data received from all parties, protecting patient healthcare information in accordance with relevant laws, and further verifies relevant licensing status of parties involved in the discharge.

20 Claims, 9 Drawing Sheets

(51) Int. Cl.
  *H04L 29/08* (2006.01)
  *H04W 4/12* (2009.01)
(52) U.S. Cl.
  CPC .......... *H04L 67/1006* (2013.01); *H04L 67/10* (2013.01); *H04W 4/12* (2013.01)

(56) References Cited

U.S. PATENT DOCUMENTS

| | | | | |
|---|---|---|---|---|
| 2008/0312972 A2* | 12/2008 | Rosow | .................... | G06Q 10/06 705/5 |
| 2013/0339040 A1* | 12/2013 | Bracken | ................. | G16H 40/20 705/2 |
| 2014/0100876 A1* | 4/2014 | Savage | .................. | G16H 10/60 705/3 |
| 2014/0316812 A1 | 10/2014 | Hathorn et al. | | |
| 2015/0213571 A1* | 7/2015 | Chambers | ............... | G06Q 10/00 705/2 |
| 2015/0310184 A1* | 10/2015 | Yui | ........................ | G16H 50/30 705/3 |
| 2016/0070712 A1* | 3/2016 | Prabhakar | ........... | G06F 16/9537 707/766 |
| 2016/0132650 A1* | 5/2016 | Kejriwal | ................ | G16H 40/20 705/2 |
| 2016/0371439 A1* | 12/2016 | Salazar | ................... | G16H 40/67 |
| 2018/0276341 A1* | 9/2018 | Rab | ...................... | G06F 21/6245 |

\* cited by examiner

130

US 11,049,607 B1

SYSTEM AND METHOD FOR FACILITATING PATIENT DISCHARGE WITH THE AID OF A DIGITAL COMPUTER

CROSS-REFERENCE TO RELATED APPLICATION

This non-provisional patent application claims priority under 35 U.S.C. § 119(e) to U.S. Provisional Patent application Ser. No. 62/500,392, filed May 2, 2017, the disclosure of which is incorporated by reference.

FIELD

This invention relates in general to electronic communications, and in particular, to a system and method for facilitating patient discharge with the aid of a digital computer.

BACKGROUND

While healthcare facilities such as hospitals offer the highest quality of a patient care, a patient generally does not stay in such a facility for an extended period of time, and eventually must be discharged. Depending on the condition of the patient, the patient may not be discharged to his or her home, and instead require admission to a long-term care facility ("LTCF"), such as a nursing home, a licensed residential care home (adult family/foster home), a skilled nursing facility, or an assisted living facility.

Currently, once the discharge date of a patient is known, the patient or a representative of the patient, such as a relative or a placement agent in a hospital, must engage in a manual search of a suitable LTCF. Generally, the patient and the patient's representative are given a stack of brochures and verbal instructions about different options. However, the patient and any representative are often under a high level of stress and neither retain a significant amount of the given instructions nor find such brochures useful.

As a result, left without a better option, the patient or the patient's representative is forced to call over the phone a large number of LTCFs in the patient's geographic area to learn availability and types of care provided in those facilities. If an LTCF has availability and provides care close to what the patient needs, the patient or the representative may visit facility in person for a tour. Such placement efforts typically takes weeks, sometimes extending to months, and such efforts may not even start until a qualified medical professional conducts an assessment of the patient necessary for the discharge. During this time, the patient generally resides in the original facility, experiencing a now-mismatched level of care, as well as confusion, stress, and possible cycles of hospital discharges and readmissions. Residing at the original facility, such as an acute care hospital, is further associated with higher costs to the hospital or to the patient than the patient would be burdened with at a suitable LTCF.

Patient discharge is further complicated due to a lack of communication between different facilities involved in the discharge, such as a hospital and an LTCF. Due to a high level of patient privacy requirements imposed by Health Insurance Portability and Accountability Act (HIPAA) as well as other similar legislations, the facilities may be unable to directly share patient data with another organization. As a result, the patient representative may be forced to physically carry the necessary documentation from one facility to another.

Accordingly, there is a need for a secure system that allows to identify a suitable facility for a patient's discharge. There is a further need for a way to provide critical information in real time about care facility availability and type of care such facilities can provide. There is a still further need for caregivers and sometimes the patients themselves to be able to access a system where important information can be securely sent to and received from medical providers.

SUMMARY

The technical and administrative difficulties as well as the long-delays associated with a conventional discharge to a long-term care facility are remedied through a system and method described below. Data from a plurality of parties involved in a discharge of the patient is securely processed in a cloud-computing environment. The cloud-computing environment identifies long-term care facilities suitable for the patient using a plurality of matching criteria derived at least in part from discharge information provided by the facility from which the patient is being, contacts the long-term care facilities to determine whether the facilities would be interested to conducting a tour for the patient's representative (and, or alternatively, the patient), and helps facilitate scheduling of the tour. The cloud-computing environment can further identify assessors capable of conducting the medical assessment of the patient and schedule the assessment, providing the assessment to all long-term care facilities that indicated willingness to conduct the tour. The cloud-computing environment securely stores the data received from all parties, protecting patient information in accordance with relevant laws, and can provide access to such information to authorized parties in near-real-time. The cloud-computing environment also verifies relevant licensing status of parties involved in the discharge to further preserve patient safety.

In one embodiment, a system and method for facilitating a patient discharge with the aid of a digital computer is provided. Information regarding a plurality of long-term care facilities and a plurality of assessors capable of performing patient medical assessments is obtained by one or more of a plurality of servers within a cloud-computing environment information, the long-term care facilities information comprising a geographic location of the long-term care facilities and care capabilities of the long-term care facilities. Discharge information for a patient is received via one of a plurality of Internetworks by one or more of the servers from a user device associated with a discharging facility, the discharge information including care needs of the patient and geographic preferences of the patient for being discharged to one of the long-term care facilities. The long-term care facility information is compared by one or more of the servers to the received discharge information and one or more of the long-term care facilities suitable for the patient are identified by the one or more servers based on the comparison. One or more requests to indicate an interest of each of the identified long-term care facility is sent by one or more of the servers to one or more user devices associated with the identified long-term care facilities via one or more of the Internetworks. A response to the request from at least one of the long-term care facilities is received by one or more of the servers via one or more of the Internetworks. A medical assessment of the patient performed by one of the assessors is provided by one or more of the servers to one or more of the user devices associated with the responding long-term care facilities. A selection of one of the responding long-term care is received by one or more of the servers from a user associated with the discharging facility, wherein the patient is discharged to the selected long-term care facility following receipt of the assessment by that long-term health care facility.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Figure 1:
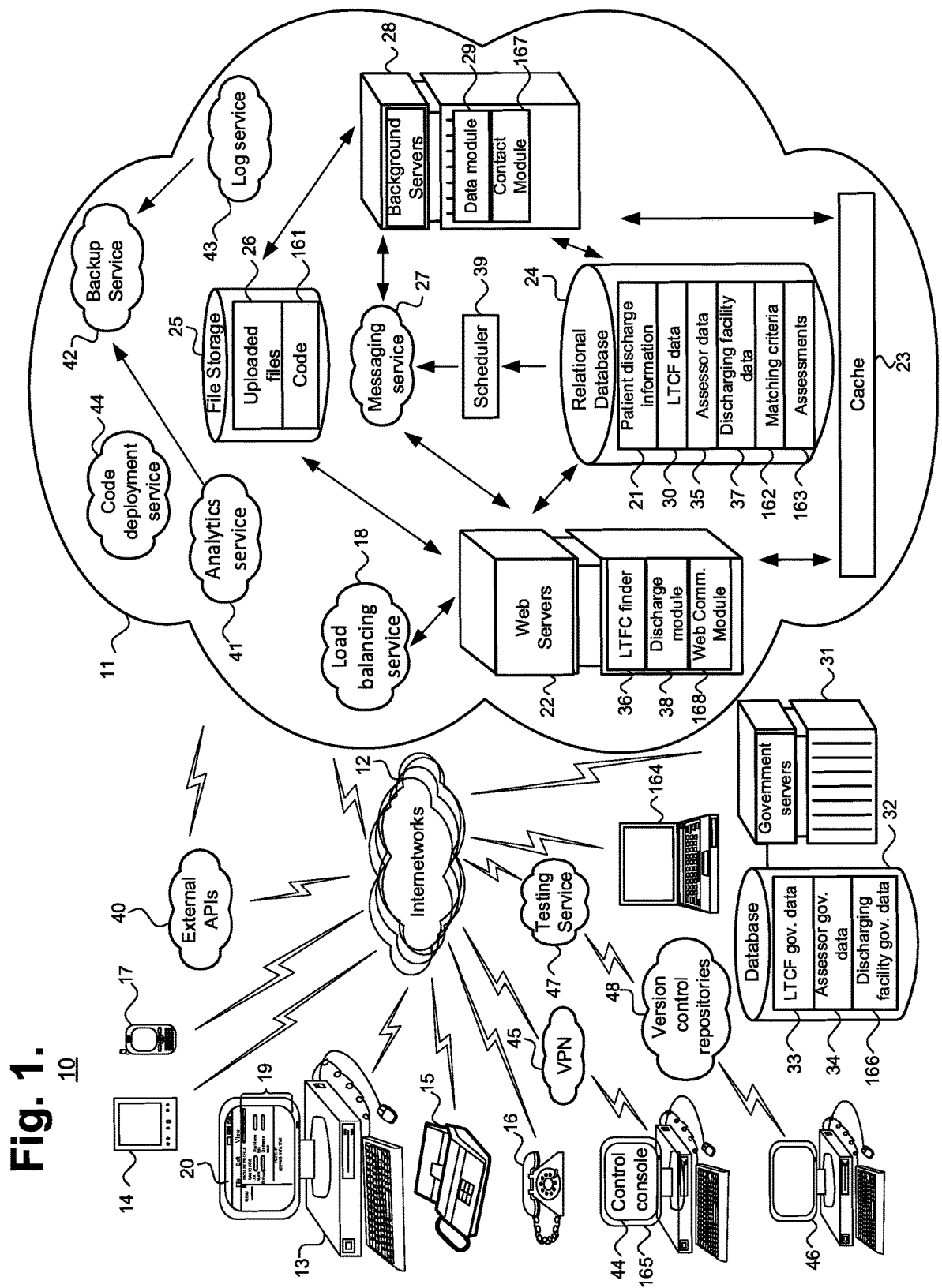
FIG. 1 is a block diagram showing a system for facilitating patient discharge with the aid of a digital computer in accordance with one embodiment.

Patient discharge can be simplified and accelerated in a secure manner through a use of the system and method described below. FIG. 1 is a block diagram showing a system 10 for facilitating patient discharge with the aid of a digital computer in accordance with one embodiment. The system includes a cloud-computing environment 11 that is interfaced to one or more Internetworks 12, such as the Internet, a cellular network, and a landline telephone network, though other kinds of Internetworks 12 are possible. Via one or more of the Internetworks 12, the cloud-computing environment 11 can communicate with a multitude of user devices 13-16 associated with parties involved in discharge of a patient and admittance of the patient to a long-term care facility (LTCF), such as a nursing home, a licensed residential care home (adult family/foster home), a skilled nursing facility, or an assisted living facility, though other kinds of LTCFs are also possible. Such user devices can include a device 13 associated with the party discharging the patient, such as a hospital. While the user device 13 is shown with reference to FIG. 1 to be a desktop computer, other kinds of user devices 13, such as laptop computers, smartphones, and tablets, are possible. Similarly, while user devices 14 and 164 are shown as a tablet and a laptop computer respectively, such devices can be other computing devices capable of connecting to one of the Internetworks.

The user-device 13 associated with the discharging facility can start a cascade of events that can lead to a discharge of the patient and an admittance of the patient to an LTCF. As further described below, the cloud-computing environment 11 provides a user interface 19 the discharging facility user device 13 can access via a web-browser 20 or a mobile application. The user interface 19 allows the discharging facility to provide to the cloud-computing environment 11 discharge information 21 for the patient. The discharge information 21 can include an identifying information of the patient being discharged, such as the patient's name and birthdate; the patient's weight; the patient's projected discharge date; the name and contact information of the patient's representative; a current location of the patient; any temporal restrictions or preferences for an assessment to be performed on the patient; a desired geographic location of an LTCF where the patient is to be admitted and a distance of an LTCF from that location that is acceptable to the patient; the desired type of an LTCF where the patient is to be admitted, such as whether the LTCF is an adult family home, an assisted living facility, or a skilled nursing facility; financial and insurance information of the patient that is relevant for the admittance of the patient to an LTCF, such as the daily rate that the patient is prepared to pay; an information about the patient's health, care needs, medications, and physical and mental abilities that are relevant to whether an LTCF can admit the patient. As part of the discharge information, a user associated with the discharging facility, such as a hospital placement agent, can upload through the user interface relevant files, such as the patient's medication lists. The discharge information 21 can also include permissions for sharing of the provided information: what parties can access particular information, such as uploaded files or contact information. Still other kinds of discharge information 21 is also possible.

In providing the discharge information 21 and other communications necessary for to facilitate the discharge of the patient, the user device 13 directly communicates with only one component of the cloud-computing environment 11. In particular, the cloud-computing environment 11 includes a load balancing service 18, which receives communications from user device 13 transmitted via one or more of the Internetworks 12, such as the Internet, and sends responses to such communications. In one embodiment, the load balancing service 18 can be one of Elastic Load Balancing products, such as an Application Load Balancer, distributed by Amazon Web Services, Inc. of Seattle, Wash.; other kinds of load balancing service 18 are also possible. Similarly, other user devices that communicate with the cloud-computing environment via the Internet, such as the user device 14 associated with assessors described below or user devices associated with LTCF 164 can further similarly communicate with the load balancing service 18 via the Internet.

The load balancing service 18 forwards the received communications to one of a plurality of web servers 22 included in the cloud-computing environment 11, assigning that web-server 22 to communicate with the user devices 13, 14, 164. In particular, each of the web-servers 22 executes a web communication module 168, which receives the communications forwarded by the load balancing service 18 and sends response communications to the user devices 13, 14, 164 via the load balancing service 18. The web servers 22 can be virtual servers or dedicated servers. In one embodiment, the web servers 22 can be an Amazon® Elastic Cloud Compute web servers provided by Amazon Web Services, Inc. of Seattle, Wash., though other kinds of the web servers 22 are also possible. When a web communication module 168 of the web-servers 22 generates a response communication for the user devices 13, 14, 164, the web communication module of the web-server 22 forwards the communication to the load balancing service 18, which in turn sends the response communication to the user device 13 via one of the Internetworks 12. The communications between the load balancing service 18 and the user devices 13, 14, 164 are encrypted to preserve the privacy of the exchanged patient data.

In communicating with the user device 13, 14, 164 a web-server 22 uses a cache 23 to store data for quick retrieval, such as session data 24 associated with a current interaction with the user device 13, 14, 164 as well as keys used in authentication of the user and encryption of the messages exchanged between the web-server 22 and the user devices 13, 14, 164. The web-server 22 also stores data received from the user devices 13, 14, 164 in persistent storage: in a relational database 24 and a file storage 25. In one embodiment, the relational database 24 can be a database that is a part of Amazon® Relational Database Service provided by Amazon Web Services, Inc. of Seattle, Wash., and implemented using MySQL 7.1, though other kinds of relational databases 24 are possible. Thus, the web communication module 168 of a web server 22 stores the discharge information 21 provided by the user device 13 into the relational database 24 with the exception of any files 26 submitted as part of the discharge information 21, which are stored in the file storage 25 along with other uploaded files 26. In one embodiment, the file storage 25 can be Amazon® S3 storage provided by Amazon Web Services, Inc. of Seattle, Wash., though other kinds of file storage are also possible. The data within the relational database 24 and the file storage 25 are encrypted to help ensure compliance with patient privacy requirements, and the use of the data requires decryption.

The web-servers 22 further communicate via a message queuing service 27 with one or more of a plurality of background process servers 28 included in the cloud-computing environment 11. In one embodiment, the message queuing service 27 can be Amazon® Simple Queue Service, though other kinds of messaging services are possible. The background process servers 28 can be virtual servers or dedicated servers. In one embodiment, the background process servers 28 can be servers that are part of Amazon Web Services® Elastic Beanstalk Worker Environments provided by Amazon Web Services, Inc. of Seattle, Wash., though other kinds of background process servers are possible.

Once a web server 22 receives and stores patient discharge information 21 and any associated files 26, a message to take action regarding the received discharge information 21 is passed from the web server 22 to one of the background process servers 28 via the message queuing service 27. Similarly, as further described below, the background process servers 28 can pass messages via the message queuing service to the web servers 22 to take action, such as contacting one of the user devices 13, 14, and 164. Likewise, both the web servers 22 and the background process servers can receive messages from a scheduler 39 within the cloud-computing environment via the message queuing service 27 with messages to take action, such as contacting a government server 31 at predefined intervals as described below or update other data that the scheduler 39 can retrieve from the relational database 24. In one embodiment, the scheduler 39 can be a Cron scheduler, though other kinds of schedulers are also possible.

Each of the background process servers 28 implements several components that enable the cloud-computing environment 11 to facilitate a discharge of the patient in response to receipt of the patient discharge information 21. Thus, each of the background process servers 28 implements a data module 29, which obtains and updates data 30 about LTCFs and data about other relevant parties necessary for facilitating the discharge. Thus, periodically, one of the background process servers 28 can contact via one of the Internetworks 12 one or more servers 31 associated with a government agency, such as of a state Department of Social and Health Services (DSHS), which are in turn interfaced to at least one database 32 storing publicly-available government data. Such government data can include information 33 regarding LTCFs such an identifier of an LTCF, such as the name and postal address of an LTCF; contact information of an LTCF, such as a phone and a fax number; and an LTCF government license number and whether the license is current; data regarding when the LTCF was inspected and inspection results; and if an inspection identified any issues, data about any citations issued to the LTCF; and an availability of licensed placement spots ("beds" hereinafter) in that LTCF. Other kinds of LTCF government information 33 is possible. As further described below beginning with the reference to FIG. 2, the data module 29 can use the LTCF government data 33 to contact and register with the cloud-computing environment 11 LTCFs, to remove LTCFs that are no longer licensed from consideration for placement, to update availability of beds within the LTCFs, and when analyzing a particular LTCF for placement of a particular patient, as further described below. The totality of information regarding LTCFs, obtained both from the government database 32 and other sources, is stored in the relational database as LTCF data 30. Additional information that is included in the LTCF data can be received from user devices 164 associated with the LTCFs, including financial information, medical skills of staff, and pictures or descriptions to be presented to potential users. As further described below with reference to FIG. 5, the availability of beds in an LTCF can be determined by using patient management software tools (not shown) employed by user devices of an LTCF that are interfaced to the cloud-computing environment 11. The number of the patients being tracked by the tools, with the tools tracking metrics such as progress notes and patient medications, is determined and is used to determine the number of beds being actually used in an LTCF, and correspondingly the number of beds available.

Similarly, data about discharging facilities 37 that have been registered with the cloud-computing environment, such as identifiers of the discharging facilities, contact information for the facilities, and licensing information for the discharging facilities is stored in the relational database 24, and can be added either by the user devices 13 or by an account manager of the account of the discharging facility associated with the cloud-computing environment 11. The active status of the government license of a discharging facility is verified prior to the registration of a discharging facility with the cloud-computing environment 11, with the registration allowing the discharge facility to input the patient discharge information 21 and trigger the cascade of events that can lead to a patient's discharge.

The government database 31 further stores other data that is necessary to facilitate a discharge. In particular, a discharge of a patient to an LTCF generally requires a medical assessment performed by an assessor, a skilled medical professional, such as a registered nurse, to make sure that the patient is fit for a discharge. Conventionally, scheduling such an assessment can take significant time, significantly delaying the discharge of the patient. The background process servers 28 can retrieve from the government database 31 government assessor information 34, such as the assessors' names, medical licensing information such as the license numbers and whether the licenses are current, and contact information. As further described below beginning with reference to FIG. 3, the government assessor information 34 is stored as part of assessor data 35 within the relational database 35 and can be used to identify licensed practitioners capable of performing the medical assessment.

Similarly, the at least one government database 31 can store discharging facility government data 166, which can include identifiers (such as names) and licensing information about a plurality of discharging facilities, such as hospitals (though other kinds of discharging facilities are possible). The government discharging facility data 166 can be used by the background processing servers 28 to verify that a discharging facility that is registered with a database is a licensed facility. The data 166 is stored as part of discharging facility data 37 within the relational database 24.

Each web server 22 further executes an LTCF finder 36 that uses the patient discharge information 21, the LTCF data 30, and the assessor data 35 to identify the LTCFs that are potentially suitable for placing the patient. As further described below in detail beginning with reference to FIG. 6, the LTCF finder 36 sets matching criteria 162 that includes at least some of the patient discharge information 21, including the desired location of the LTCF and a range from that location acceptable for placement (which can be expressed as a radius, though other measures of distance are possible) and the healthcare needs of the patient. The set of matching criteria 162 further includes the availability of beds in the LTCFs being considered; and the criteria that the LTCF must have been previously registered with the cloud-computing environment 11. Other criteria are possible. The LTCF finder 36 executes a search of the LTCF data 30 to identify LTCFs at least partially satisfying the matching criteria: LTCFs within the desired geographic range that can at least partially match the patient's healthcare needs, have availability of beds, and have been registered with the cloud-computing environment 11. If no matching LTCFs are identified, the matching criteria 162 are modified and the search is repeated one or more times with the modified matching criteria until either matching LTCFs are found or no more modifications are permitted. For example, initially, the modifying of the matching criteria involves increasing the search range by a predefined amount one or more times as long as the search range remains below a predefined threshold (such as being within the boundaries of the state where the patient is located, though other thresholds are also possible). Once the predefined threshold has been reached, the search range is returned to the original value, but one of the criteria is dropped from the matching criteria set 162 and the search is repeated. In one embodiment, the dropped criteria can be the availability of beds (though other criteria being dropped first are possible), and an LTCF can be found suitable even if the LTCF currently is not known to have available beds. If no matching LTCFs are found with the availability criteria dropped, the range is increased and the search is repeated as described above one or more times until the range increases beyond the predefined threshold. If no matching LTCFs are found, another criteria is dropped for the set, the requirement for LTCFs to be registered with the cloud-computing environment 11, and the search range is returned to the original value, and the search is repeated: an LTCF that has not previously been registered with the cloud-computing environment, but data about which is obtained from the government database 32. If no matching LTCFs are found with the availability criteria dropped, the range is increased and the search is repeated as described above one or more times until the range increases beyond the predefined threshold as described above. If no matches are identified, the background server 28 performing the matching notifies the user device 13 through the web server 22 assigned to communicate with the user device 13 and the elastic balancing service 18 to contact an account manager associated with the system.

After the matching LTCFs are identified, the matching LTCFs are contacted by a contact module 167 implemented by each of the background process servers 28. As further described below with reference to FIG. 8, the contact module 167 contacts each of the identified matching LTCFs with a request to indicate whether these LTCFs are interested in having the patient, the patient representative, or both conduct a tour of the LTCF (which is also indicative of the desire of the LTCF to have that patient placed in that LTCF). In a further embodiment, instead of requesting to indicate whether an LTCF is willing to schedule a tour, other indications of the LTCF to have that patient placed in the LTCF can be included in the communication sent to the LTCFs by the contact module 167. The LTCFs can be contacted via a plurality of communication channels, with the LTCFs being contacted via different communication channels if they do not respond to the initial communications via a first communication channel. Such communication channels can include a cellular phone 17 of an individual associated with the LTCF, a voicemail associated with the cell phone, a fax machine 15 associated with the LTCF, and a landline phone 16 associated with the LCTF. Other channels are possible. For example, the contact module can send an SMS message to the LTCFs if the contact information for sending the message is available. Likewise, the communications themselves can be automatically generated voice messages or text messages. The messages are delivered via the Internetworks 12 by External APIs 40 with which the contact module 167 interfaces. A positive or negative response can be received via the same communication channel through which the communication was sent or via a different communication channel. For example, when receiving a call via a cell phone or landline, an LTCF employee responding to the call can press a button on the cell phone or the landline phone to indicate a positive or negative response. On the other hand, after receiving a fax, the recipient can call a provided number to respond to the received message. The received responses are presented to the user via the user interface 20, and upon receiving a user selection of one or more of the LTCFs, the contact module 167 can either contact the selected LTCF via one of the External APIs 40 to schedule the tour at a time received from the user, or can provide to the user contact information of the LTCF to allow the user to schedule the tour directly.

In a further embodiment, in addition to a simple indication of the willingness to conduct a tour, the responses received from LTCFs can include a rate at which they would be willing to admit the patient. The LTCFs can also be notified by the contact module 167 about rates that one or more other LTCFs responded with and be given an opportunity to change their rate one or more time. Thus, the LTCFs are allowed to place bids on admitting the patient by communicating their rates to the web servers 22 and modify such rates.

If matching LTCFs are found and have responded affirmatively to request to conduct the tour, information about the matching LTCFs is transmitted to the user device 13 by one of web communication module of one of the web servers 22 via the load balancing service 18 and are presented to the user. An LTCF is considered a match if the matching criteria 162 even by 1%: that is an LTCF that is within a searched geographic area and that satisfies availability and registration criteria, if they are used, and that is at least a partial match to the medical needs of the patient included in the discharge information 21, is a match that can be presented to the user. In determining the degree of match, some of the patient's healthcare needs can be weighed heavier than others. For example, if the patient is diabetic and is also prescribed therapeutic massage, an LTCF that has staff capable of administering insulin shots but no on-site massage therapist could receive a higher match percentage than an LTCF that has an on-site massage therapist, but no staff capable of administering insulin shots.

The presented information can include the name and location of an LTCF, the available beds in that LTCF; languages spoken in that LTCF; and how much a particular LTCF matches the matching criteria 162, such as percent match. The order in which the matching LTCFs are presented can be determined in a variety of ways, including the degree to which the LTCFs match the matching criteria 162, an alphabetical order, the distance between the LTCFs and the location included in the discharge information, and a history of the cloud-computing environment's 11 interaction with the LTCFs. Other ways to sort the results are possible.

Each of the web-servers further executes a discharge module 38, which can take additional steps to facilitate patient discharge. While a third party (such as the cloud-computing environment 11) may not be always permitted to schedule an assessment of the patient due to limitations of the patient's insurance plan, the discharge module 38 of the web-servers 22 and the contact module 167 of the background process servers 28 can also schedule an assessment of the patient by a skilled medical professional to allow the discharge of the patient to be completed, as further described below beginning with reference to FIG. 2. Whereas conventionally, LTCFs are not contacted until the assessment is performed, the discharge module 38 schedules the assessment at approximately the same time as the suitable LTCFs are identified and contacted. As mentioned above, the assessor data 35 includes the temporal availability and the geographic region where the assessors performs the assessment, and the discharge module 38 can identify assessors capable of performing the assessment at the nearest future by comparing the assessor data to the patient location and temporal preferences or restrictions included in the discharge information 21. The discharge module 38 requests the contact module 167 of one of the background process servers, the web communication module 168 of one of the web servers, or both, to contact multiple identified assessors at the same time, sending messages either via the External APIs 40 or via the load balancing service 18 to user devices 14 of the assessors to indicate whether they will perform the assessment at a specific location during a specific temporal interval. The assessor can send the message from the user devices 14 to indicate that they will perform the assessment. Upon receiving the indication from one of the assessors, the discharge module 38 will contact the other contacted assessors with additional messages to let them know that their response is no longer needed. The discharge module 38 will also provide the patient discharge information 21 to the assessor who will perform the assessment via a web communication module 168 of one of the web servers.

While or after performing the assessment, the assessor can communicate the results of the assessment to the discharge module 38 by either filling out an assessment form, which can be either a file locally stored on the user device 14 or be provided through the web-browser 20 or a mobile application executing on the user device 14, with the form being served by one of the web-servers 22 via the load balancing service 18. The web-browser 20 or the mobile application can also present to the assessor a messaging service, such as a chat box, through which the assessor can send messages to the discharging facility (such as the user device 13) and receive answers, which may further facilitate the assessment. The received assessments 163 are stored by one of the web-servers 22 in the relational database 24 (or possibly as one of the uploaded files 26 in the file storage 25), and is subsequently provided by the discharge module 38 via the web-communication module of one or more of the web servers 22 to all the LTCFs that indicated their willingness to have the patient or the representative of the patient tour that LTCF.

Following the tour, the user associated with the user device 13 of the discharging facility notifies the web communication module 168 of the web-server 22 communicating with the user device 13 if one of the suggested LTCFs is selected. The communication module 168 of the web-servers 22 further receive via one of the Internetworks 12 from user devices 164 associated with the selected LTCFs a confirmation from the selected LTCF that the patient has been discharged to that LTCF. The confirmation and the user can be stored in the relational database 24, such as in the discharge information 21 of the patient.

The cloud-computing environment 11 provides an easy way for a system administrator to control the implementation and configuration of the components of the environment. In particular, the cloud-computing environment can present an analytics service interfaced to all components of the cloud-computing environment 11 that can monitor and analyze the activities of the components. In one embodiment, the analytics service 41 be Amazon® Cloudwatch provided by Amazon Web Services, Inc. of Seattle, Wash., though other analytics services are possible. A system administrator use a control console 44 running on user device 165 connected to a virtual private network 45 (VPN) interfaced to one of the Internetworks 12 can configure the cloud-computing environment 11 and receive the data from the analytics service 41. In a further embodiment, the virtual private network 45 can be omitted.

A system administrator or another developer can also deploy code within the cloud-computing environment 11 from a user device 46 via a code deployment service 44 and the file storage 25 within the cloud-computing environment 11. In one embodiment, the code deployment service 44 can be AWS CodeDeploy provided by Amazon Web Services, Inc. of Seattle, Wash., though other deployment services are possible. In particular, the code to be deployed is initially passed from the user device 46 of the developer to a version control repository 48, such a server implementing the Git version control system as well as, or alternatively, Bitbucket® servers implanting Jira® software, both provided by Atlassian Pty Ltd proprietary limited company of Sydney, Australia, though other version control repositories are possible. Subsequently, the code is transmitted to a testing service 48, such as Bitbucket® Pipelines service, where the code is tested to identify potential issues. Following the testing, the code is stored within the file storage 25, and the code deployment service 44 is notified that the code has been stored, which triggers the code deployment service 44 to retrieve and deploy the code throughout the cloud-computing environment.

The cloud-computing environment 11 further includes a log service 43, which is interfaced to all other components of the cloud computing environment and which all of the transactions that take place within the cloud-computing environment 11. Thus, the created logs include when particular data from the relational database 24 or the file storage 25, allowing to know when and by whom information about a particular patient was accessed, which promotes security of the patient's information. In one embodiment, the logging service 43 can be DynamoDB provided by Amazon Web Services, Inc. of Seattle, Wash., though other logging services are possible.

The log service 43 and the analytics service 41 are interfaced with at least one backup service 42, which backs up all the data within the cloud-computing environment 11 (being interfaced to them via the connection to the analytics service 41), including the logs created by the logging service 43. In one embodiment, the backup service 42 can be Amazon® Glacier provided by Amazon Web Services, Inc. of Seattle, Wash., though other backup services are also possible. In a further embodiment, the backup service 42 service can interface with a secondary backup service (not shown), which can be located outside of the cloud-computing environment 11, such as Microsoft Azure®, provided by Microsoft Corporation of Redmond, Wash., though other secondary backup services are possible.

As mentioned above, the communications between the load balancing service 18 and the user devices 13, 14, 164 are encrypted to preserve the privacy of the exchanged patient data. Similarly, all data being exchanged and stored within the cloud-computing environments 11 is encrypted, including data exchanged between servers 22 and 28, the scheduler 39, and the data stored within and transmitted from the file storage 25 and relational database 24, the backup service 44, the cache 23, and other components. Similarly, communications sent to the External APIs 40 by the background process servers 28 and received from the External APIs 40 by the background servers are similarly encrypted.

The servers 22, 28, as well as user devices 13, 14, 164, 165, 46 can include components conventionally found in programmable computing devices, such as one or more CPUs, memory, input/output ports, network interfaces, and non-volatile storage, although other components are possible. The servers 22, 28 can each include one or more modules for carrying out the embodiments disclosed herein. The modules can be implemented as a computer program or procedure written as source code in a conventional programming language and that is presented for execution by the central processing unit as object or byte code. Alternatively, the modules could also be implemented in hardware, either as integrated circuitry or burned into read-only memory components, and each of the servers 22, 28 can act as a specialized computer. For instance, when the modules are implemented as hardware, that particular hardware is specialized to perform the communications and analysis that other computers without the hardware cannot be used for that purpose. The various implementations of the source code and object and byte codes can be held on a computer-readable storage medium, such as a floppy disk, hard drive, digital video disk (DVD), random access memory (RAM), read-only memory (ROM) and similar storage mediums. Other types of modules and module functions are possible, as well as other physical hardware components.

Further components, referred to as "services" in the description above, such as services 18, 27, 44, 42, 43 include servers and database necessary for implementing those servers.

Still other components are possible in the system. For example, patients and their caregivers may use personal devices to access data that is provided to the user devices 13 via the load-balancing service 18.

In a still further embodiment, the components of the cloud-computing environment described above, such as the load balancing service 18, the servers 22 and 28, the scheduler 39, the file storage 25, the relational database 24, the backup service 42, the analytics service 41, the code deployment service 44, the message queuing service 27, the cache 23, the log service 43, can be located in a centralized location, such as on premises of a hospital, instead of being in the cloud-computing environment 11.

Figure 2:
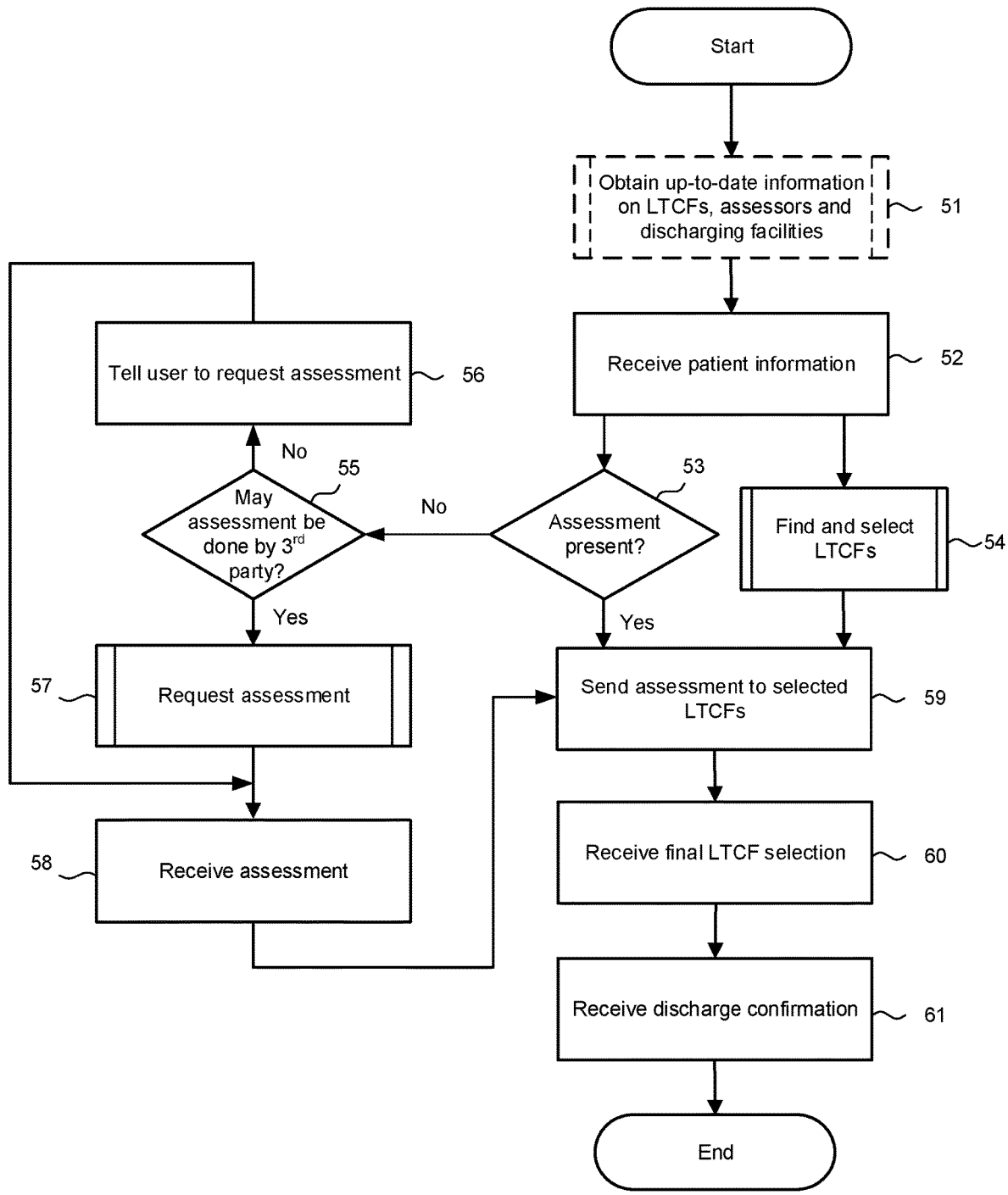
FIG. 2 is a flow diagram showing a method for facilitating patient discharge with the aid of a digital computer in accordance with one embodiment.

By coordinating data exchange from a plurality of parties involved in patient discharge in a secure and efficient manner, patient discharge can be significantly accelerated and costs associated with discharge delays significantly reduced. FIG. 2 is a flow diagram showing a method 50 for facilitating patient discharge with the aid of a digital computer in accordance with one embodiment. The method 50 can be implemented using the system 10 of FIG. 1, though other implementations are also possible.

Figure 3:
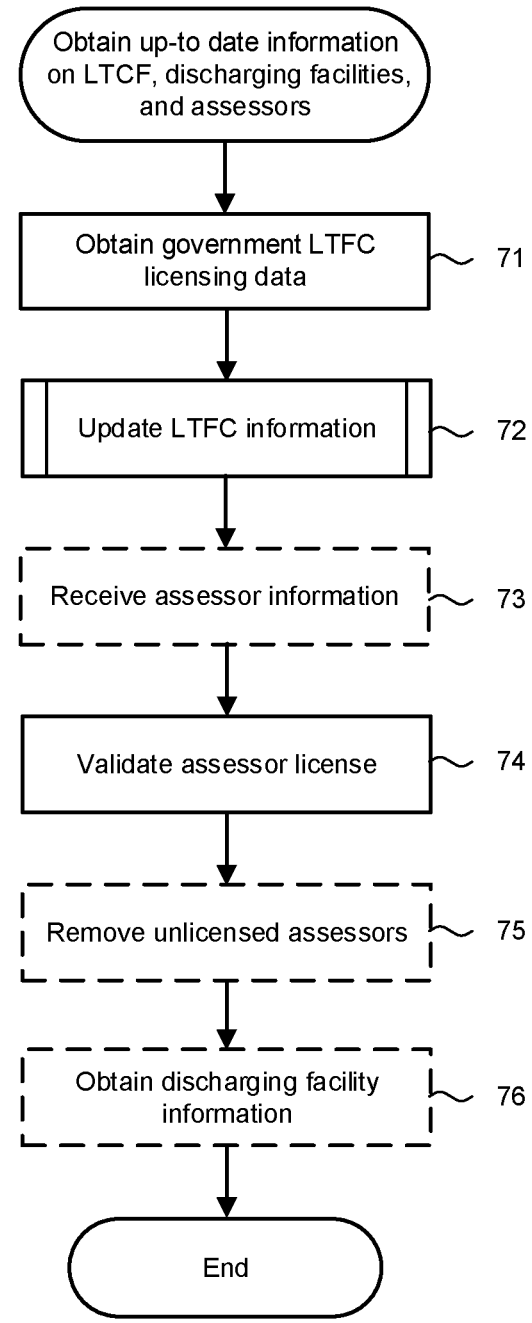
FIG. 3 is a routine for obtaining up-to-date information on LTCFs, discharging facilities, and assessors for use in the method of FIG. 2 in accordance with one embodiment.

Optionally, if not already present, up-to-date information on LTCFs, assessors, and discharging facilities is obtained by the background processing servers (step 51), as further described below beginning with reference to FIG. 3. Patient discharge data is received from a user device associated with the discharging facility via a load balancing service by one of the web servers (step 52). LTCFs suitable for admitting the patient are identified by the web server and tours are scheduled with one or more of the LTCFs using one of the background processing servers (step 53), as further described below with reference to FIG. 7. At the same time as the scheduling of the tours, one of the web servers determines if an assessment of the patient for the discharge has previously been done and provided to the cloud-computing environment (step 53). If the assessment has been done and the results are accessible to the web server (step 53), the method 50 moves to step 59. If the results of the assessment are not accessible to the web server, the web server determines if a third party (such as the web server) is allowed to schedule the assessment (step 55), which may not be always possible due to administrative restrictions of the patient's healthcare plan. If the web server cannot schedule the assessment (step 55), the web server sends a message to a user device associated with the discharging facility with a request to schedule the assessment (step 56) and the method 50 moves to step 58. If the cloud-computing environment can schedule the assessment (step 55), the web server schedules the assessment using one of the background process servers, as further described below with reference to FIG. 9. The assessment is received by the web server (step 58), either from a user device associated with the assessing nurse or from a user device associated with the discharging facility, and the assessment will be made available to LTCFs selected by the user associated with the discharging facility, such as via logging in by the individual user into a web application maintained by the web communication module of the web servers (step 59). A user selection for discharge of the patient to one of the LTCFs is received from a user device associated with the discharging facility (step 60) and a discharge confirmation is received from a user device associated with the LTCF selected for placement (step 61), ending the method.

While performance of the patient medical assessment is often required by law in many jurisdictions prior to a discharge of the patient to an LTCF, in a further embodiment of the method 50, the steps relating to the assessment and provision of the assessment to the LTCF can be omitted and a patient discharge can be facilitated without the assessment being performed.

Obtaining up-to-date information on the LTCFs, assessors, and the discharging facilities allows to determine effective ways to contact these entities and make sure that no unlicensed parties are involved in the discharge of the patient in roles where government licensing is necessary. FIG. 3 is a routine 70 for obtaining up-to-date information on LTCFs, discharging facilities, and assessors for use in the method 50 of FIG. 2 in accordance with one embodiment. Initially, publicly-available government data for LTCS (such as an identifier of an LTCF, license number, inspection and citation data, status of the license, and expiration date of the license, contact information for the LTCF, information about availability of beds, and contact information of the owner of the LTCF) and assessors is obtained by one of the background process servers from one or more government servers via an Internetwork (step 71). Obtaining such government data can be done on a recurring basis, such as every day.

Figure 4:
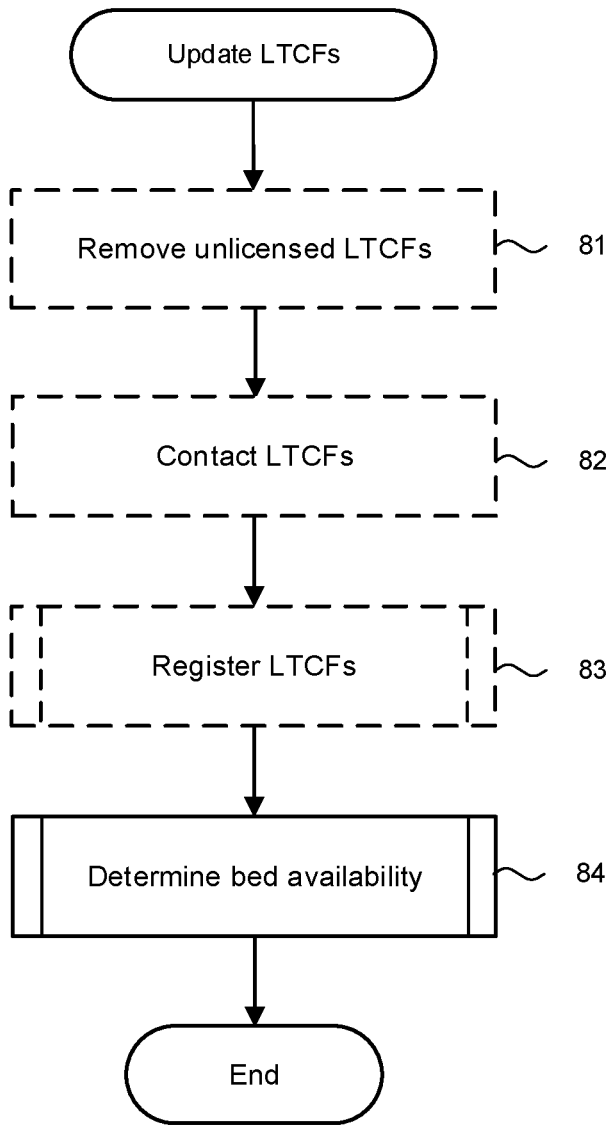
FIG. 4 is a flow diagram showing a routine for updating LTCFs for use in the routine of FIG. 3 in accordance with one embodiment.

LTCF data in the relational database is updated based on the obtained government information by one or more of the background process servers (step 72), as further described below with reference to FIG. 4.

Optionally, information of assessors wishing to register with the cloud-computing environment, such as the assessors name, license number, and contact information is received by the cloud-computing environment (such as by one of the web servers), such as from user devices associated with such assessors, though other sources are also possible, and stored in the relational database and possibly in the file storage (step 73). The licenses of all of the assessors whose information is stored in the relational database is validated using the information retrieved from the government servers by one or more of the background process servers (step 74), and any assessors whom the data obtained from the government servers does not show having a valid license are removed by one or more of the background process servers from the list of assessors who could be contacted to schedule a patient assessment (step 75). Finally, optionally, information about discharging facilities is received from these discharging facilities, such as by one of the web servers via the load balancing service, and from the government database, and if the discharging facility is shown to have an up-to-date government license (as verified by the information retrieved from the government database, the discharging facility is registered with the cloud-computing environment (allowing the discharging facility to provide patient discharge information and receive the matching LTCFs) and the information about the discharging facility is stored in the relational database (step 76), ending the routine 70. The information about the discharging facilities can be received by the cloud-computing environment from the user devices associated with these discharging facilities, such as via the load balancing service, or be provided to a system user (such as an account manager) and input into the cloud-computing environment.

Using up-to-date LTCF information allows to avoid contacting LTCFs who are no longer licensed for their services. FIG. 4 is a flow diagram showing a routine 80 for updating LTCFs for use in the routine 70 of FIG. 3 in accordance with one embodiment. The routine 70 can be performed by one or more of the background process servers, with web servers being employed as described below. Optionally, if a comparison of the government information to information within the relational database shows any of the LTCFs as no longer licensed, the LTCFs are removed from a list of the LTCFs considered for possible discharge of the patient (step 81). Optionally, LTCFs whose information has been received from the government server are contacted, either by the web servers or the background processing server depending on the way of communication employed, with an invitation to register with the cloud-computing environment (step 82). Optionally, if one or more of the contacted LTCFs respond to the invitation, the LTCFs are added by one or more background process servers or web servers to the list of registered LTCFs within the relational database (step 83), as further described with reference to FIG. 6. Bed availability of one or more LTCFs registered with the cloud-computing environment is subsequently determined (step 84), as further described below with reference to FIG. 5, ending the routine 80.

Figure 5:
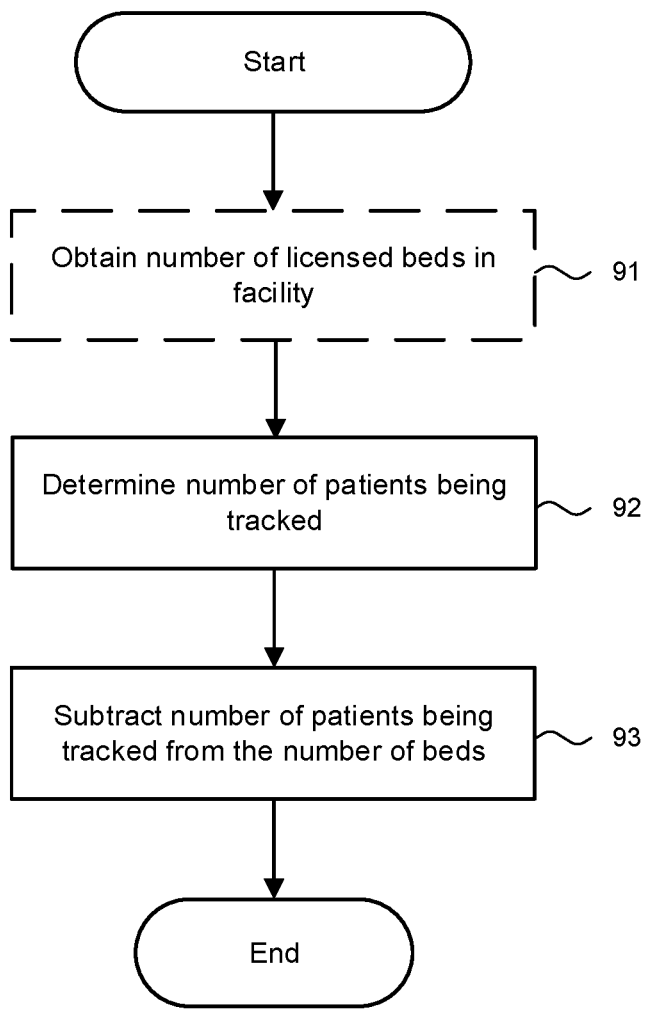
FIG. 5 is a flow diagram showing a routine for determining availability of beds in an LTCF for use in the routine of FIG. 4 in accordance with one embodiment.

While the registered LTCFs periodically update the number of licensed beds available in those LTCFs with the cloud-computing environment, such information may be out-of-date and not useful in finding matching LTCFs when the availability of beds is one of the criteria used. As described above, user devices used by LTCFs can use patient management tools software interfaced to the web servers via one of the Internetworks, which can be used to track a variety of patient-related metrics, such as progress notes, and the medications that a particular patient is taking (though other metrics are possible), and report the tracked data to the cloud-computing environment; the number of patients being tracked can be used to determine the availability of beds in an LTCF. FIG. 5 is a flow diagram showing a routine 90 for determining availability of beds in an LTCF for use in the routine 80 of FIG. 4 in accordance with one embodiment. Initially, optionally, if not already available, a number of beds an LTCF that has been provided during the LTCF registration is retrieved by one of the background process servers (step 91). The number of patients for whom the tracking software is used is determined by the background process server (step 92). The number of available beds is determined by the background process server by subtracting the number of patients for whom medications are being tracked from the total number of beds in that LTCF (step 93), ending the routine.

Figure 6:
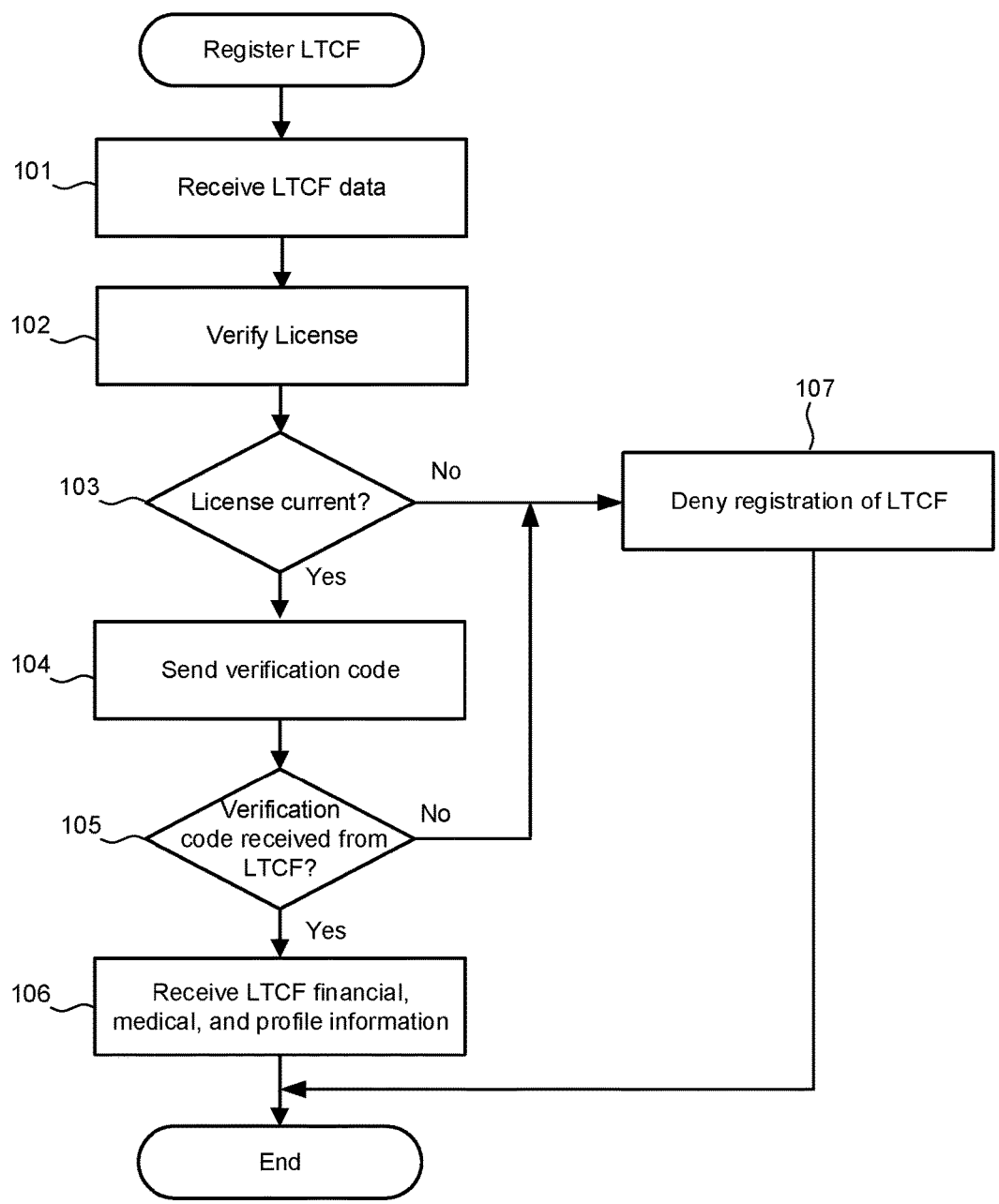
FIG. 6 is a flow diagram showing a routine for registering an LTCF with the cloud-computing environment in accordance with one embodiment.

Registering an LTCF with the cloud-computing environment requires to verify that communications purportedly being received from that LTCF are genuine. FIG. 6 is a flow diagram showing a routine 100 for registering an LTCF with the cloud-computing environment in accordance with one embodiment. Initially, registration data is received from an LTCF that includes the name of the owner of the LTCF, an identifier (such as a name) of the LTCF, licensing information of the LTCF, and contact information of the LTCF by one of the web servers (step 101). Whether the license of the LTCF is current is determined by the web server using the licensing information obtained from the government server (and maintained in the relational database) (step 102), and if the LTCF's licensed is not determined verified (step 103), the LTCF is denied registration and is removed from the list of LTCF that are considered for a patient being discharged into (step 107), ending the routine 100. If the license has been verified as current (step 103), a verification code is sent by one of the background servers via one of the External APIs to contact information of the LTCF that is present in the data retrieved from the government database (step 104). In one embodiment, the verification code is sent by one of the background process servers via one or more of the External APIs to at least one of a landline phone number and a fax number associated with the LTCF, though in a further embodiment, other communication channels can be used. If an individual associated with the LTCF transmits the verification code back to the cloud-computing environment (105), either via the same or different communication channel than the one used to transmit the verification code, the information being received for the registration of the LTCF is determined to be genuinely coming from the LTCF, and the registration is completed by receiving from the LTCF additional data, such as financial and billing information of that LTCF, additional medical information associated with the LTCF, and allowing the LTCF to provide profile information, such as a textual description and an image that can be displayed to a user associated with discharging facility when information about the LTCF is presented (step 106), ending the routine 100. If no verification code is received within a predefined amount of time, then the registration is denied (step 107), ending the routine 100, as the user with whom the cloud-computing environment was initially interacting lacks access to the communication devices whose contact information is provided to the government and is thus likely not associated with the LTCF.

Figure 7:
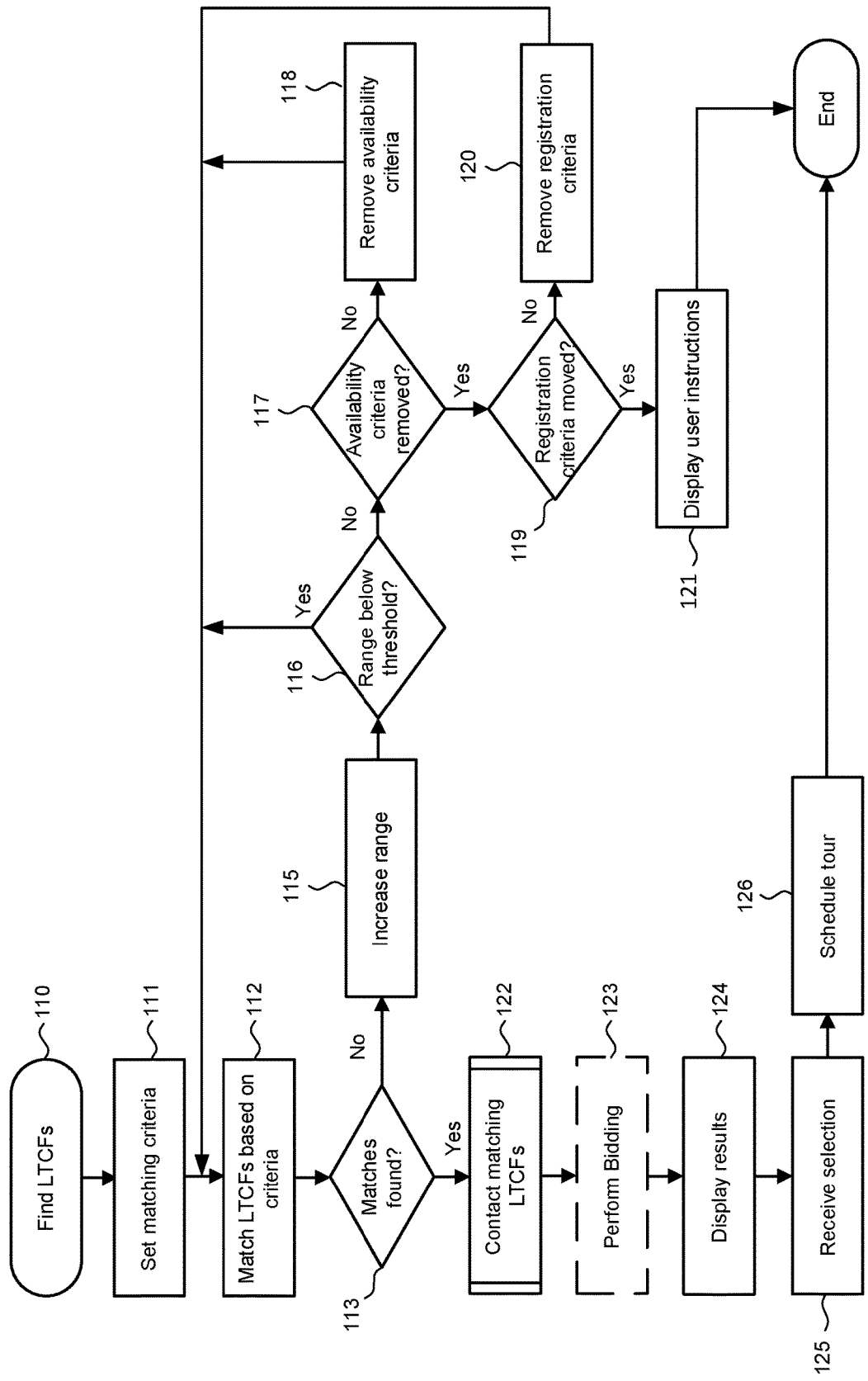
FIG. 7 is a flow diagram showing a routine for finding LTCFs suitable for the discharge of the patient for use in the FIG. 2 in accordance with one embodiment.

Taking into account multiple matching criteria allows to find LTCFs most suited for placement of the patient. FIG. 7 is a flow diagram showing a routine 110 for finding LTCFs suitable for the discharge of the patient for use in the FIG. 2 in accordance with one embodiment. Initially, a set of matching criteria is obtained by one of the web servers (step 111). The matching criteria can include a requirement for availability of beds within an LTCF, a requirement that an LTCF is registered with the cloud-computing environment, the medical care needs of the patient, the desired geographic location of an LTCF and a permissible distance range from the desired location. Other criteria are possible.

The LTCFs are matched to the matching criteria by the web server by comparing the data associated with the LTCFs, such as location, registration availability of beds, and medical care capabilities of the LTCF are compared to the matching criteria, to identify LTCFs that at least partially match patient discharge needs (step 112). If no matches are found (step 113), the range is increased by the web server by a predefined amount (step 115). Whether the range is below the threshold (such as the area covered by that range being without the geographic boundaries of the patient is located) is determined by the web server, and if the range is below the threshold (step 116), the routine 110 returns to step 112 and another match is performed. If the range exceeds the threshold (step 116), whether the availability of beds criteria has been removed from the matching criteria is determined by the web server (step 117). If the availability of beds criteria has not been removed (step 117), the availability criteria is removed from the set of matching criteria by the web server and the range is restored to the value set at the beginning of the routine 110 by the web server (step 118), and the routine returns to step 112, where another match is performed by the web server using the modified matching criteria. If the availability of beds criteria has previously been removed from the matching criteria set (step 117), whether the requirement for the matching LTCFs to be registered with the cloud-computing environment has been removed as a criteria is determined by the web server (step 119). If the registration requirement has not previously been removed from the matching criteria set (step 119), the registration criteria is removed by the web server from the matching criteria set and the range is restored to the value set at the beginning of the routine 110 by the web server (step 120) and the routine 110 returns to step 112, where another match is performed by the web server using the modified matching criteria. If the registration criteria has already been removed from the set of matching criteria (step 119), the user who provided the discharge information is sent a message by the web server to contact his or her account representative as no suitable matches could be found (step 121). In a further embodiment, additional steps can be performed by the web servers 121 to attempt to contact and register additional LTCFs if the registration criteria has already been removed in step 119 without sending the message to contact the account manager.

Figure 8:
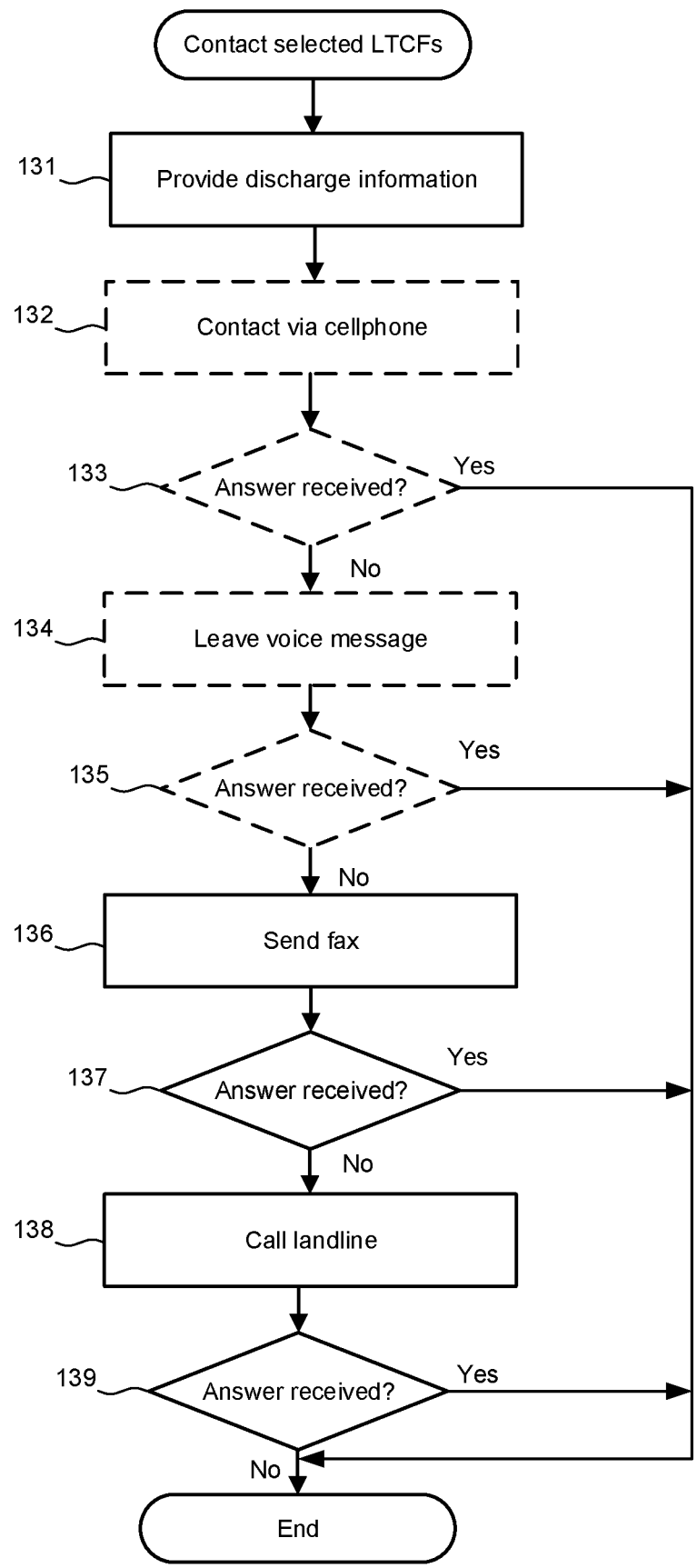
FIG. 8 is a flow diagram showing a routine for contacting matching LTCFs for use in the routine of FIG. 7 in accordance with one embodiment.

As further described above with reference to FIG. 1, if even partial matches are identified by the web server (step 113), the matching LTCFs are contacted by one or more of the background servers via the External APIs to indicate whether they would be willing to have the patient or the representative of the patient tour that LTCF (step 122), as further described below with reference to FIG. 8. In a further embodiment, the contacted LTCFs are asked to provide other information indicating whether or not they are interested in placing the patient within the particular LTCFs. Optionally, in addition to the providing an answer to whether they are interested to have the patient tour the facility (or other indication of interest to admit the patient), the contacted LTCFs can indicate a rate at which they would be willing to admit the patient to that LTCF; the LTCFs can also be notified via, for example, the same communication channel through which they provided the bid by one of the background process servers or one of the web servers, the rate quoted by other LTCFs and allowed to modify their rate, thus effectively allowing the LTCFs to bid for the placement of the patient (step 123). Following the expiration of a predefined period of time, information about those matching LTCFs that have responded that they are willing to have the patient or the representative tour (or otherwise indicated interest in having the patient admitted to) that LTCFs is displayed to a user associated with the discharging facility (124). The displayed information can include the degree to which the LTCF match the matching criteria, the location of the LTCF, the number and kind of beds in that LTCF, and the medical care capabilities of that LTCF, though other displayed information is possible. The order in which the LTCFs are displayed can be based on a variety of factors, including the degree to which the LTCF match the matching criteria, the daily rate of those LTCFs, and previous interactions with those LTCFs. Other ways to sort the information about the LTCFs are possible.

A user selection of one or more of the displayed LTCFs is received (step 125) and arrangements for scheduling a tour of the selected LTCFs are made (step 126), ending the routine 120. In one embodiment, the cloud-computing environment can provide the user associated with the discharging facility the contact information of a selected LTCF to allow the user to schedule the tour. In a further embodiment, the cloud-computing environment can directly contact the selected LTCF and schedule a tour at a time received from the user that is also acceptable to the LTCF.

The background process servers can contact matching LTCFs in a variety of ways to maximize the chance of receiving the response. FIG. 8 is a flow diagram showing a routine 130 for contacting matching LTCFs for use in the routine 120 of FIG. 7 in accordance with one embodiment. While the description below references contacting one of the LTCFs, multiple LTCFs can be contacted in the same way simultaneously by the background process servers via the External APIs. Initially, at least a portion of the discharge information regarding the patient is provided via to all of the matching LTCFs, such as via being available on a webpage that the users associated with an LTCF can access via one of the Internetworks, the load balancing service, and the web servers; other ways of providing the information are possible, such as sending e-mails or faxes to addresses associated with the LTCFs by the background servers via one or more of the External APIs (step 131). Optionally, if a cellular phone number of an LTCF is available, one or more of the background process servers contacts via the External APIs a cellular phone associated with each of the LTCFs with a voice message (generated by the background process or the External APIs) to check the discharge information about the patient and to indicate whether the LTCF is willing to have the patient or the patient representative tour that LTCF (or in a further embodiment, to otherwise indicate interest in admitting the patient) (step 132). If a representative of the LTCF who answers the call provides a positive or a negative answer (such as by pressing a button on the cell phone, with the instructions to do so being included in the message) (step 133), the routine 130 ends. If no answer is received (step 133), optionally, depending on whether the initial call was placed, the generated voice-message is left at the voicemail box associated with the cell phone (step 134). If the LTCF provides an answer to one of the background servers or one of the web servers via one of the Internetworks within a predefined amount following the leaving of the voice message (step 135), the routine 130 ends. If no answer is received within a predefined amount of time (step 135), or if the steps 131-134 were not performed, the background process server sends via one of the External APIs a fax to a fax number associated with the LTCF, with the fax including the same content as described above with reference to the voice message (step 136). If a response from the LTCF is received during a predefined amount of time following the sending of the fax (step 137), the routine 130 ends. If the response is not received within a predefined amount of time (137), the background process server sends the voice message via one of the External APIs to a landline phone associated with the LTCF (step 138). The routine 130 regardless of whether the answer is received within a predefined period of time following the initiation of the call to the landline (step 139).

Figure 9:
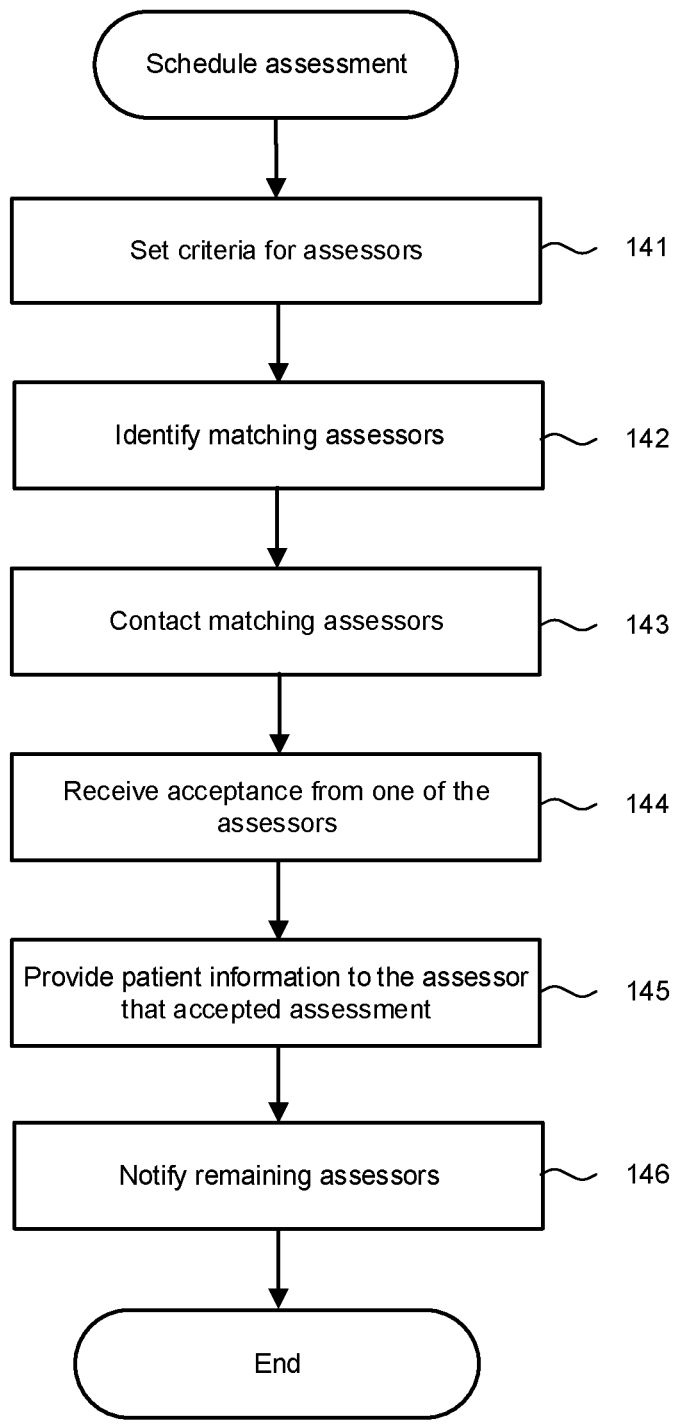
FIG. 9 is a flow diagram showing a routine for scheduling an assessment of the patient for use in the method of FIG. 2 in accordance with one embodiment.

Arranging an assessment of the patient while also identifying the LTCFs where the patient can be discharged allows to accelerate the discharge of the patient. FIG. 9 is a flow diagram showing a routine 140 for scheduling an assessment of the patient for use in the method of FIG. 2 in accordance with one embodiment. A set of criteria for selecting the assessors is set by one of the web servers based on the received patient discharge information (step 141). The criteria includes the geographic location of the patient who needs to be assessed and the desired time for the assessment to be performed (which can be obtained from the patient's discharge information). One or more assessors whose geographic availability for performing assessments and temporal availability, as recorded in the assessor data in the relational database, matches the assessor selection criteria are identified by one of the web server (step 142). The matching assessors are contacted by one or more of the background processing servers, either through one or more web-servers or through the External APIs, with a message to provide a response via their user devices whether that assessor will perform the patient assessment at a specified time and location (step 143). The response that one of the assessors will perform the assessment is received from that assessor by the background process server or the web server (step 144), and the discharge information regarding the patient is provided to the assessor that responded by one or more of the background servers via the External APIs or by the web server, such as via being available on a webpage that the assessor can access by logging in via one of the Internetworks, the load balancing service, and a web servers; other ways of providing the information are possible, such as by e-mailing the discharge information to the assessor, though still other ways to provide the information are possible (step 145). The remaining assessors are notified by the background process server or the web server that their response is no longer needed as the assessment has been scheduled (step 146), ending the routine 140.

While in the description above, the discharging facility is referred to as a hospital, in a further embodiment, the patient could use the system and method described above to personally select a LTCF and be "discharged" into that LTCF from the patient's home, with the user device 13 being associated with the patient or the patient's non-hospital representative. Further, the discharging facility referenced in the system and method above can be any state licensed medical facility, including an LTCF looking to discharge a patient to another LTCF.

While the invention has been particularly shown and described as referenced to the embodiments thereof, those skilled in the art will understand that the foregoing and other changes in form and detail may be made therein without departing from the spirit and scope of the invention.

What is claimed is:

1. A method for facilitating a patient discharge with aid of a digital computer, comprising:

obtaining, by one or more of a plurality of background process servers comprised within a cloud-computing environment, information regarding a plurality of long-term care facilities located in multiple states and a plurality of assessors capable of performing patient medical assessments, the long-term care facilities information comprising a geographic location of each of the long-term care facilities within one of the multiple states and care capabilities of the long-term care facilities;

receiving, via one of a plurality of Internetworks, by a load balancing service comprised within the cloud-computing environment and implemented by one or more servers, from a user device associated with one of a plurality of discharging facilities, each discharging facility located in one of the multiple states, encrypted discharge information for one of a plurality of patients, each patient located in one of the multiple states, the discharge information comprising care needs of the patient and geographic preferences of the patient for being discharged to one of the long-term care facilities;

providing, by the load balancing service, the received discharge information to one of a plurality of web servers comprised within the cloud computing environment, and assigning, by the load balancing service, to the one of the plurality of web servers to perform encrypted communication with the user device that provided the encrypted discharge information, wherein the web servers and the background process servers communicate via a message queuing service comprised within the cloud computing environment, and wherein the web server stores session data regarding the encrypted communication and keys used for the encrypted communication within the cloud-computing environment;

obtaining by one or more of the background process servers an up-to-date availability of placement spots in the long-term care facilities and adding the up-to-date availability of the placement spots to the long-term care facilities information, comprising interfacing, via one or more of the Internetworks, patient management tools software associated with each of the long-term care facilities, determining a number of long-term care facility patients being tracked by the patient management tools software associated with each of the long-term care facilities, and setting the number of the long-term care facility patients being tracked by patient management tools software associated with each of the long-term care facilities as a number of the long-term care facility patients currently in those long-term care facilities, wherein the patient management tools software are executing outside of the cloud-computing environment;

comparing, by the web server, the long-term care facility information to matching criteria, the matching criteria comprising a set of criteria comprising the received discharge information and a requirement for the placement spots being available;

identifying, by the web server, one or more of the long-term care facilities suitable for the patient based on the comparison;

sending, by one or more of the background process servers, to one or more user devices associated with each of the identified long-term care facilities, using one or more external APIs, via one or more of the Internetworks, one or more requests to indicate an interest of each respective long-term care facility in admitting the patient;

receiving, by one or more of the background process servers, via one or more of the Internetworks, a response to the request from at least one of the long-term care facilities;

causing at least in part the patient to be discharged to one of the responding long-term care facilities by one or more of the web servers comprising providing a patient medical assessment of the patient performed by one of the assessors to one or more of the user devices associated with the responding long-term care facilities;

receiving, by the web server, via one or more of the Internetworks, from the user device associated with the discharging facility, a selection of one of the long-term care facilities that provided the; and receiving by one or more of the web servers from one of the user devices associated with the selected long-term care facility a confirmation that the patient has been discharged to the selected long-term care facility.

2. A method according to claim 1, further comprising two or more of:

delivering one of the requests to cellular phones associated with each of the long-term care facilities;

upon not receiving the responses from one or more of the cellular phones during a time period, leaving a voice message in a mailbox associated with the cellular phones that have not responded;

sending one of the requests to faxes associated with each of the long-term care facilities from whom the response has not been received; and upon not receiving the responses from one or more of the long-term care facilities associated with the faxes following an additional time period, delivering one of the requests to a landline phone number associated with each of the long-term care facilities that have not provided the response following the sending of the requests to the faxes.

3. A method according to claim 1, further comprising:

retrieving, by one or more of the background process servers, from one or more servers associated with a government agency, government data associated with each of the plurality of long-term care facilities, the government data comprising licensing information of each of the long-term care facilities, an identifier of each of the long-term care facilities, an availability of openings within each of the long-term care facilities, and contact information of each of the long-term care facilities;

registering by one or more of the background servers at least one of the one or more of the long-term care facilities, comprising:

contacting the at least one long-term care facility with an invitation to provide registration information, the registration information comprising the identifier of the contacted long-term care facility; and receiving the registration information from the contacted long-term care facility;

verifying a licensing status of the contacted long-term care facility using the licensing information and the identifier;

providing a verification code to the contact information comprised within the government data; and receiving the verification code from the at least one long-term care facility, wherein the registration is completed following receipt of the verification code.

4. A method according to claim 3, wherein the registration information further comprises a total number of the placement spots within the contacted long-term care facility, obtaining the up-to-date availability of the placement spots in the long-term care facilities further comprising:

subtracting the number of the long-term care facility patients currently in each of the long-term care facilities from the total number of the placement spots in the same long-term care facility; and setting a result of subtraction for each of the long-term care facilities as a number of available placement spots within the same long-term care facility.

5. A method according to claim 1, further comprising:

setting the matching criteria, wherein the geographic preferences comprise a geographic range from a location associated with the patient;

upon none of the long-term care facilities satisfying the matching criteria, modifying the matching criteria by increasing the geographic range, comparing the increased geographic range to a threshold, and upon the increased geographic range being below the threshold, comparing the long-term care facility information and the availability of the placement spots at the long-term care facilities to the modified matching criteria; and upon the increased geographic range being above the threshold, changing the matching criteria by removing the requirement for the placement spots being available from the set, decreasing the increased geographic range, and comparing the long-term care facility information to the changed matching criteria.

6. A method according to claim 1, wherein the set of the criteria further comprises an availability of placement spots within each of the long-term care facilities and whether each of the long-term care facilities have been registered with the cloud-computing environment.

7. A method according to claim 1, wherein the assessor information comprises geographic ranges within which each of the assessors perform the assessments and temporal availability of the assessors to perform the assessments, further comprising:
  receiving assessor matching criteria comprising a temporal interval for the assessment and a location of the patient;
  comparing the assessor information for the plurality of the assessors to the assessor matching criteria and identifying those of the assessors suitable for performing the assessment of the patient based on the comparison;
  contacting the identified assessors with a request to perform the assessment;
  receiving an acceptance of the request to perform the assessment from one of the assessors and providing the discharge information to the assessor that accepted the request;
  notifying the remaining identified assessors of the acceptance; and
  receiving the assessment from the one assessor.

8. A method according to claim 7, wherein the one assessor receives the discharge information via at least one of a mobile application and a web-browser executing on a mobile device of the one assessor.

9. A method according to claim 1, further comprising:
  scheduling a tour of the selected long-term care facility, wherein the patient is discharged to the selected long-term care facility after the tour.

10. A method according to claim 1, wherein the information regarding the plurality of long-term care facilities and the plurality of assessors is updated by the one or more of the background process servers daily.

11. A system for facilitating a patient discharge with aid of a digital computer, comprising:
  a cloud computing environment, comprising:
    background process servers configured to obtain information regarding a plurality of long-term care facilities located in multiple states and a plurality of assessors capable of performing patient medical assessments, the long-term care facilities information comprising a geographic location of each of the long-term care facilities within one of the multiple states and care capabilities of the long-term care facilities;
    a load balancing service comprised within the cloud computing environment and implemented by one or more servers, the load balancing service configured to:
      receive, via one of a plurality of Internetworks, from a user device associated with one of a plurality of discharging facilities, each discharging facility located in one of the multiple states, encrypted discharge information for one of a plurality of patients, each patient located in one of the multiple states, the discharge information comprising care needs of the patient and geographic preferences of the patient for being discharged to one of the long-term care facilities;
      provide the received discharge information to one of a plurality of web servers comprised within the cloud computing environment; and
      assign to the one of the plurality of web servers to perform encrypted communication with the user device that provided the encrypted discharge information, wherein the web servers and the background process servers communicate via a message queuing service comprised within the cloud computing environment, and wherein the web server stores session data regarding the encrypted communication and keys used for the encrypted communication within the cloud-computing environment;
    one or more of the background process servers configured to obtain an up-to-date availability of placement spots in the long-term care facilities and add the up-to-date availability of the placement spots to the long-term care facilities information, comprising interfacing, via one or more of the Internetworks, patient management tools software associated with each of the long-term care facilities, determining a number of long-term care facility patients being tracked by the patient management tools software associated with each of the long-term care facilities, and setting the number of the long-term care facility patients being tracked by patient management tools software associated with each of the long-term care facilities as a number of the long-term care facility patients currently in those long-term care facilities, wherein the patient management tools software are executing outside of the cloud-computing environment;
    the web server configured to compare the long-term care facility information to matching criteria, the matching criteria comprising a set of criteria comprising the received discharge information and a requirement for the placement spots being available;
    the web server configured to identify one or more of the long-term care facilities suitable for the patient based on the comparison;
    one or more of the background process servers configured to send to one or more user devices associated with each of the identified long-term care facilities, using one or more external APIs, via one or more of the Internetworks, one or more requests to indicate an interest of that long-term care facility in admitting the patient;
    one or more background process servers configured to receive, via one or more of the Internetworks, a response to the request from at least one of the long-term care facilities;
    one or more of the web servers configured to cause at least in part the patient to be discharged to one of the responding long-term care facilities comprising providing a patient medical assessment of the patient performed by one of the assessors to one or more of the user devices associated with the responding long-term care facilities; and
    the web server configured to receive, via one or more of the Internetworks, from the user device associated with the discharging facility, a selection of one of the long-term care facilities that provided the response; and
    one or more of the web servers configured to receive from one of the user devices associated with the selected long-term care facility a confirmation that the patient has been discharged to the selected long-term care facility.

12. A system according to claim 11, the cloud-computing environment configured to perform two or more of:
   deliver one of the requests to cellular phones associated with each of the long-term care facilities;
   upon not receiving the responses from one or more of the cellular phones during a time period, leave a voice message in a mailbox associated with the cellular phones that have not responded;
   send one of the requests to faxes associated with each of the long-term care facilities from whom the response has not been received; and
   upon not receiving the responses from one or more of the long-term facilities associated with the faxes following an additional time period, deliver one of the requests to a landline phone number associated with each of the long-term care facilities that have not provided the response following the sending of the requests to the faxes.

13. A system according to claim 11, the cloud-computing environment further comprising:
   one or more of the background process servers configured to receive, from one or more servers associated with a government agency, government data associated with each of the plurality of long-term care facilities, the government data comprising licensing information of each of the long-term care facilities, an identifier of each long-term care facility, an availability of openings within each of the long-term care facilities, and contact information of each of the long-term care facilities;
   one or more of the background process servers configured to register at least one of the one or more of the long-term care facilities, comprising:
      contact the at least one long-term care facility with an invitation to provide registration information, the registration information comprising the identifier of the contacted long-term care facility; and
      receive the registration information from the contacted one long-term care facility;
      verify a licensing status of the contacted long-term care facility using the licensing information and the identifier;
      provide a verification code to the contact information comprised within the government data; and
      receive the verification code from the contacted long-term care facility, wherein the registration is completed following receipt of the verification code.

14. A system according to claim 13, wherein the registration information further comprises a total number of the placement spots within the contacted long-term care facility, one or more of the background process servers further configured to:
   subtract the number of the long-term care facility patients currently in each of the long-term care facilities from the total number of the placement spots in the same long-term care facility; and
   set a result of subtraction for each of the long-term care facilities as a number of available placement spots within the same long-term care facility.

15. A system according to claim 11, the cloud computing environment configured to:
   set the matching criteria, wherein the geographic preferences comprise a geographic range from a location associated with the patient;
   upon none of the long-term care facilities satisfying the matching criteria, modify the matching criteria by increasing the geographic range, compare the increased geographic range to a threshold, and upon the increased geographic range being below the threshold, comparing the long-term care facilities to the modified matching criteria; and
   upon the increased geographic range being above the threshold, changing the matching criteria by removing the requirement from the set for the placement spots being available, decreasing the increased geographic range, and comparing the long-term care facility information to the changed matching criteria.

16. A system according to claim 11, wherein the set of the criteria further comprises an availability of placement spots within each of the long-term care facilities and whether each of the long-term care facilities have been registered with the cloud-computing environment.

17. A system according to claim 11, wherein the assessor information comprises geographic ranges within which each of the assessors perform the assessments and temporal availability of the assessors to perform the assessments, the cloud computing environment further configured to:
   receive assessor matching criteria comprising a temporal interval for the assessment and a location of the patient;
   compare the assessor information for the plurality of the assessors to the assessor matching criteria and identifying those of the assessors suitable for performing the assessment of the patient based on the comparison;
   contact the identified assessors with a request to perform the assessment;
   receive an acceptance of the request to perform the assessment from one of the assessors and providing the discharge information to the assessor that accepted the request;
   notify the remaining identified assessors of the acceptance; and
   receive the assessment from the one assessor.

18. A system according to claim 17, wherein the one assessor receives the discharge information via at least one of a mobile application and a web-browser executing on a mobile device of the one assessor.

19. A system according to claim 11, the cloud computing environment further configured to:
   schedule a tour of the selected long-term care facility, wherein the patient is discharged to the selected long-term care facility after the tour.

20. A system according to claim 11, wherein the information regarding the plurality of long-term care facilities and the plurality of assessors is updated by the one or more of the background process servers daily.

* * * * *